US00PP27183P3

(12) United States Plant Patent
Trees

(10) Patent No.: US PP27,183 P3
(45) Date of Patent: Sep. 20, 2016

(54) ***SALVIA* PLANT NAMED 'BLACK AND BLOOM'**

(50) Latin Name: *Salvia guaranitica*
Varietal Denomination: Black & Bloom

(71) Applicant: Ball Horticultural Company, West Chicago, IL (US)

(72) Inventor: Scott Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 125 days.

(21) Appl. No.: 14/544,479

(22) Filed: Jan. 12, 2015

(65) Prior Publication Data
US 2016/0205859 P1 Jul. 14, 2016

(51) Int. Cl.
*A01H 5/02* (2006.01)

(52) U.S. Cl.
USPC ..... Plt./475

(58) Field of Classification Search
USPC ..... Plt./475
See application file for complete search history.

*Primary Examiner* — June Hwu
(74) *Attorney, Agent, or Firm* — Audrey Charles

(57) ABSTRACT

A new and distinct cultivar of *Salvia* plant named 'Black & Bloom', characterized by its dark violet-blue colored flowers, dark green-colored foliage, and vigorous, upright growth habit, is disclosed.

2 Drawing Sheets

Latin name of genus and species of plant claimed: *Salvia guaranitica.*

Variety denomination: 'Black & Bloom'.

BACKGROUND OF THE INVENTION

The present invention relates to a new and distinct cultivar of *Salvia* plant botanically known as *Salvia guaranitica* and hereinafter referred to by the cultivar name 'Black & Bloom'.

The new cultivar originated in a controlled breeding program in Arroyo Grande, Calif. during September 2009. The objective of the breeding program was the development of a *Salvia* cultivar having large violet-blue colored flowers and dark green colored foliage.

The new *Salvia* cultivar is the result of cross-pollination. The female (seed) parent of the new cultivar is 'Costa Rican Blue', not patented, characterized by its dark blue-colored flowers, dark green-colored foliage, and highly vigorous, upright growth habit. The male (pollen) parent of the new cultivar is 'Black & Blue', not patented, characterized by its medium violet-blue colored flowers, medium green-colored foliage, and moderately vigorous, upright growth habit. The new cultivar was discovered and selected as a single flowering plant within the progeny of the above stated cross-pollination during December 2010 in a controlled environment in Arroyo Grande, Calif.

Asexual reproduction of the new cultivar by terminal stem cuttings since December 2010 in Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Black & Bloom' as a new and distinct cultivar of *Salvia* plant:

1. Dark violet-blue colored flowers;
2. Dark green-colored foliage; and
3. Vigorous, upright growth habit.

Plants of the new cultivar differ from plants of the female parent primarily in having a more violet flower color and reduced growth vigor.

Of the many commercially available *Salvia* cultivars, the most similar in comparison to the new cultivar is the male parent 'Black & Blue', not patented. However, in side by side comparisons, plants of the new cultivar differ from plants of 'Black & Blue' in at least the following characteristics:

1. Plants of the new cultivar are taller than plants of 'Black & Blue';
2. Plants of the new cultivar have darker colored leaves than plants of 'Black & Blue'; and
3. Plants of the new cultivar have a more rugose leaf texture than plants of 'Black & Blue'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Black & Bloom'. The plants were grown in 4-inch pots for 4 weeks then 6-inch pots for 4 weeks in a greenhouse in West Chicago, Ill. Plants were given one pinch at first transplant.

DETAILED BOTANICAL DESCRIPTION

Figure 1:
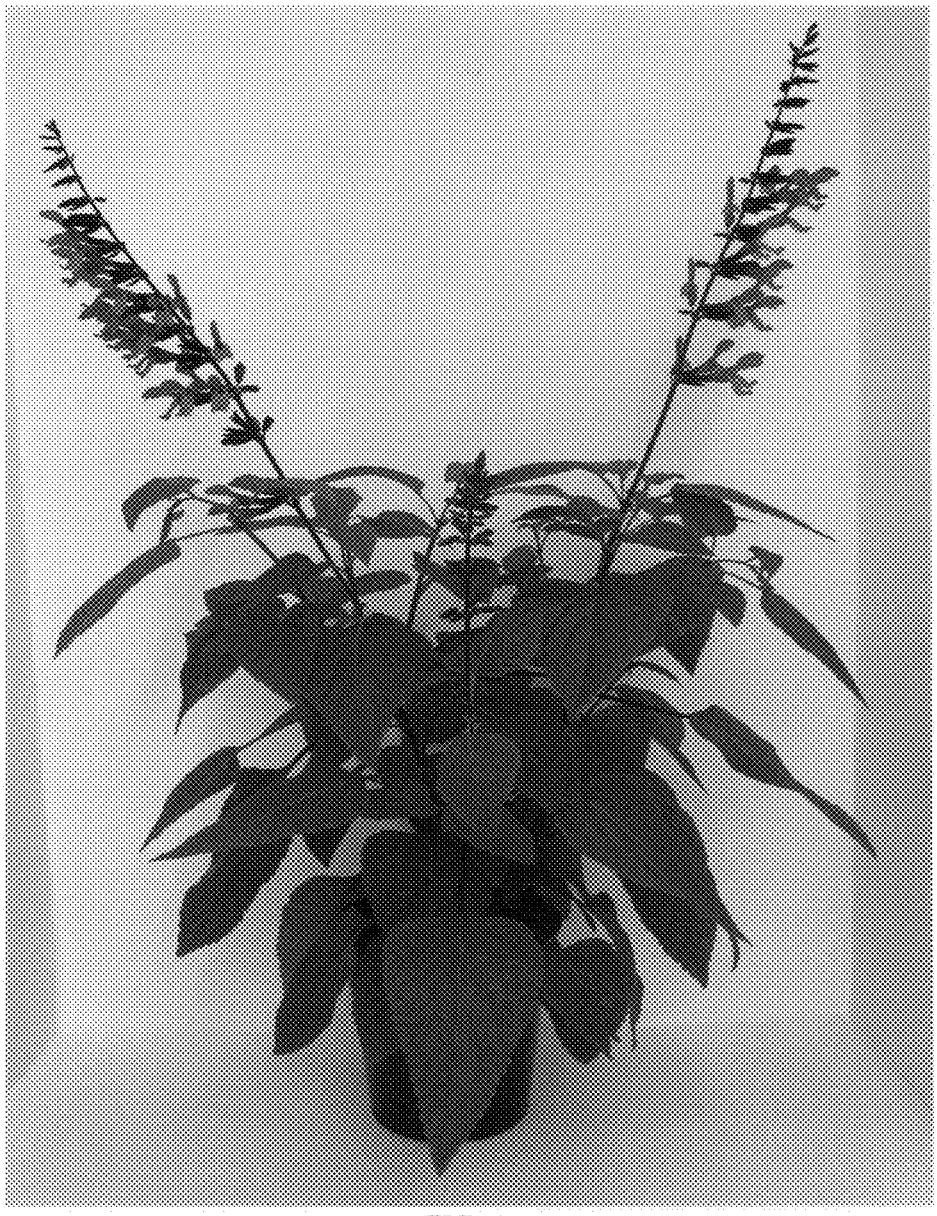
FIG. 1 illustrates a side view of the overall growth and flowering habit of 'Black & Bloom'.
Figure 2:
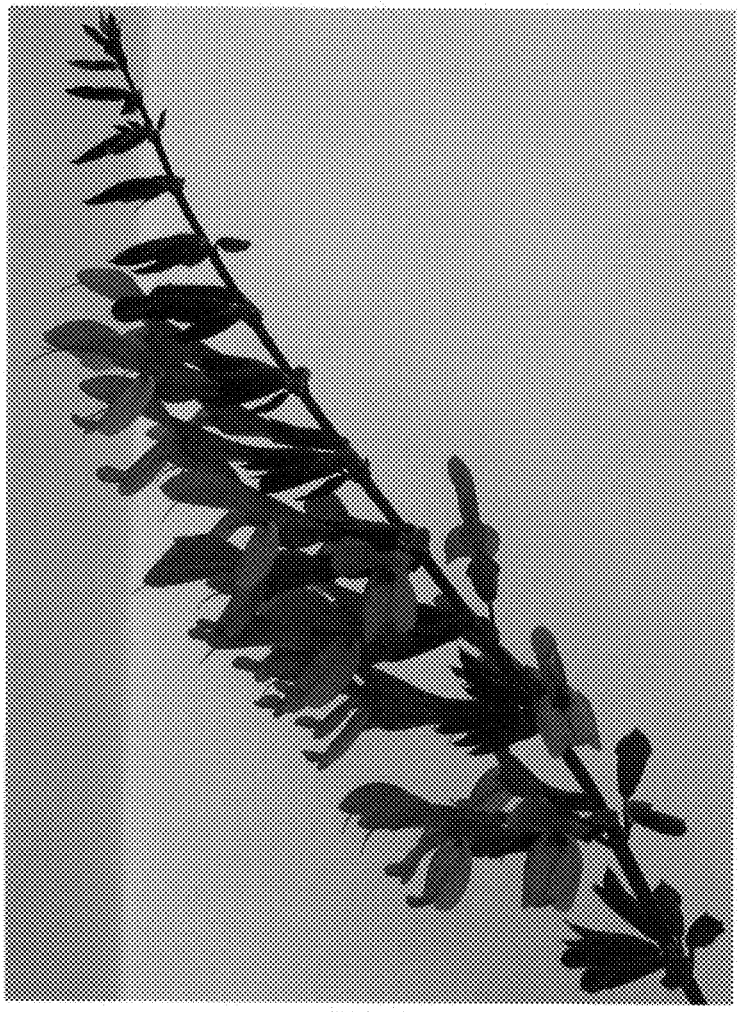
FIG. 2 illustrates a close-up view of an inflorescence of 'Black & Bloom'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in November 2014 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 4 weeks then 6-inch pots for 4 weeks in a greenhouse utilizing a soilless growth medium. Plants were given one pinch at transplant. Greenhouse temperatures were maintained at approximately 66° F. to 70° F. (19° C. to 21° C.) during the day and approximately 58° F. to 62° F. (14° C. to 17° C.) during the night. Greenhouse light levels of 2,500 footcandles to 6,000 footcandles were maintained during the day. Measurements and numerical values represent averages of typical plants.

Botanical classification: *Salvia guaranitica* cultivar Black & Bloom.

Parentage:

*Female parent*.—'Costa Rican Blue', not patented.

*Male parent*.—'Black & Blue', not patented.

Propagation:

*Type cutting*.—Terminal stem.

*Time to initiate roots*.—Approximately 6 to 9 days.

*Time to produce a rooted cutting*.—Approximately 21 to 28 days.

*Root description*.—Medium thickness, fibrous, brown in color.

*Rooting habit*.—Freely branching.

Plant description:

*Commercial crop time*.—Approximately 8 to 10 weeks from a rooted cutting to finish in a 15 cm pot.

*Growth habit and general appearance*.—Vigorous, upright growth habit.

*Size*.—Height from soil level to top of plant plane: Approximately 72.0 cm. Width: Approximately 60.0 cm.

*Branching habit*.—Freely branching. Pinching enhances lateral branching. Quantity of branches per plant: Approximately 2 main basal branches and approximately 16 lateral branches.

*Branch*.—Shape: Square in cross section. Strength: Strong. Length to base of inflorescence: Approximately 35.0 cm. Diameter: Approximately 7.0 mm. Length of central internode: Approximately 8.0 cm. Texture: Moderately pubescent. Color of young and mature stems: 146A with a heavy overlay of N186A.

Foliage description:

*General description*.—Quantity of leaves per main branch: Approximately 12. Fragrance: Strong, sage-like. Form: Simple. Arrangement: Opposite.

*Leaves*.—Aspect: Acute to perpendicular angle to stem. Shape: Ovate to deltoid. Margin: Crenate. Apex: Acute. Base: Truncate to slightly oblique. Venation pattern: Pinnate. Length of mature leaf: Approximately 15.0 cm. Width of mature leaf: Approximately 10.5 cm. Texture of upper surface: Rugose, sparsely pubescent. Texture of lower surface: Rugose, densely pubescent. Color of upper surface of young foliage: 137A with 139A and venation of 147B. Color of lower surface of young foliage: Closest to N137D with venation of 146C. Color of upper surface of mature foliage: N137A with 139A and venation of 147B. Color of lower surface of mature foliage: Closest to N137D with venation of 146C.

*Petiole*.—Length: Approximately 7.5 cm. Diameter: Approximately 4.0 mm. Texture: Moderately pubescent. Color: 146A with a heavy overlay of N186A.

Flowering description:

*Flowering habit*.—'Black & Bloom' is freely flowering under outdoor growing conditions with substantially continuous blooming from spring through autumn and year-round in greenhouse environment.

*Lastingness of individual floret*.—Approximately 4 to 5 days.

Inflorescence description:

*General description*.—Type: Spikes in verticillaster arrangement, florets in clusters of five, not persistent. Quantity of inflorescences per plant: Approximately 2. Fragrance: Faint, sweet. Length or height of inflorescence: Approximately 27.0 cm. Width of inflorescence: Approximately 8.5 cm. Quantity of fully-open flowers per inflorescence: Approximately 25.

*Peduncle*.—Shape: Square in cross section. Strength: Strong. Aspect: Erect. Length: Approximately 9.5 cm. Diameter: Approximately 4.0 mm. Texture: Densely glandular pubescent. Color: N186A.

Flower description:

*Type*.—Single, zygomorphic.

*Bud*.—Rate of opening: Generally takes 2 to 3 days for bud to progress from first color to fully open flower.

*Bud just before opening*.—Shape: Obovoid. Length: Approximately 2.1 cm. Diameter: Approximately 5.0 mm. Texture: Moderately pubescent. Color: Calyx of N186A and petals of N92B.

*Corolla*.—Shape: Bilabiate, lower lip having three lobes, base fused. Width: Approximately 1.0 cm. Length: Approximately 2.1 cm. Depth: Approximately 4.8 cm.

*Upper lip*.—Shape: Hooded. Margin: Entire. Apex: Rounded. Length from throat: Approximately 2.0 cm. Width: Approximately 3.0 mm. Texture of inner surface: Glabrous. Texture of outer surface: Moderately pubescent. Color of inner surface when first and fully open: 94B. Color of outer surface when first and fully open: N89C.

*Lower lip*.—Shape of central lobes: Oblong. Margin: Entire. Apex of central lobe: Emarginate. Apex of lateral lobes: Rounded. Length from throat of central lobe: Approximately 1.6 cm. Width of central lobe: Approximately 6.0 mm. Length from throat of lateral lobes: Approximately 1.3 cm. Width of lateral lobes: Approximately 3.0 mm. Texture of upper surface: Glabrous. Texture of lower surface: Sparsely pubescent. Color of upper surface when first and fully open: N89C. Color of lower surface when first and fully open: N89D.

*Corolla tube*.—Length: Approximately 2.8 cm. Diameter at opening: Approximately 3.0 mm. Diameter at base: Approximately 2.0 mm. Texture of inner and outer surfaces: Glabrous. Color of inner surface when first and fully open: 94B with base of NN155C. Color of outer surface when first and fully open: N89B with base of NN155C.

*Calyx*.—Shape: Tubular. Length: Approximately 1.7 cm. Diameter: Approximately 7.0 mm.

*Sepals*.—Quantity per flower: Fused into two lobes. Shape: Obovate. Apex: Upper lobe acute, lower lobe notched. Length: Approximately 1.7 cm. Width of lobes: Approximately 7.0 mm. Texture of inner and outer surfaces: Moderately pubescent. Color of inner surface: N137A with an overlay of N186A on upper half. Color of outer surface: N186A.

*Bracts*.—Quantity: One bract located at the base of floret cluster. Texture of inner surface: Glabrous. Texture of outer surface: Moderately pubescent. Color of inner surface: N137A with an overlay of N186A on upper half. Color of outer surface: N186A.

*Pedicel*.—Strength: Strong, flexible. Aspect: At an acute angle. Length: Approximately 6.0 mm. Diameter: Approximately 1.0 mm. Texture: Densely pubescent. Color: N186A.

*Reproductive organs*.—Androecium: Stamen quantity: 2 per flower, dorsifixed, strongly curved. Stamen length: Approximately 2.3 cm. Filament length: Approximately 2.0 mm. Filament color: N89B with base of N89A. Anther shape: Oblong. Anther length: Approximately 5.0 mm. Anther color: N89A. Pollen amount: Abundant. Pollen color: NN155A. Gynoecium: Pistil quantity: 1 per flower, slightly curved. Pistil length: Approximately 5.1 cm. Stigma shape: Cleft, two-parted. Stigma length: 5.0 mm. Stigma color: N89B. Style length: Approximately 4.3 cm. Style color: NN155D, with an overlay of N89B that fades toward ovary. Style texture: One longitudinal line of hairs colored N89B. Ovary length: Approximately 3.0 mm. Ovary color: 18D.

Seed and fruit production: Neither seed nor fruit production has been observed.

Disease and pest resistance: Resistance to pathogens and pests common to *Salvia* has not been observed.

What is claimed is:

1. A new and distinct cultivar of *Salvia* plant named 'Black & Bloom', substantially as herein illustrated and described.

* * * * *